United States Patent [19]

Cichra et al.

[11] 4,452,739

[45] Jun. 5, 1984

[54] 1,3,3,5,7,7-HEXANITROPERHYDRO-1,5-DIAZOCINE, N-NITROSO ANALOGS THEREOF, AND PROCESSES FOR THEIR PREPARATION

[75] Inventors: Dorothy A. Cichra; Horst G. Adolph, both of Silver Spring; Mortimer J. Kamlet, Rockville, all of Md.

[73] Assignee: The United States of America as represented by the Secretary of the Navy, Washington, D.C.

[21] Appl. No.: 481,042

[22] Filed: Mar. 31, 1983

[51] Int. Cl.³ ............................................. C07D 245/02
[52] U.S. Cl. ................................. 260/239 BC; 149/88
[58] Field of Search ................................... 260/239 BC

[56] References Cited

U.S. PATENT DOCUMENTS 3,228,928  1/1966  Frankel ........................ 260/239 BC
3,926,953  12/1975  Coburn et al. ............... 260/239 BC Primary Examiner—Paul M. Coughlan, Jr.
Assistant Examiner—D. B. Springer
Attorney, Agent, or Firm—Robert F. Beers; Kenneth E. Walden; Roger D. Johnson

[57] ABSTRACT

Nitroorganic compounds of the formula

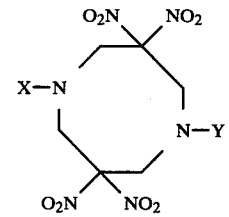

wherein x and y may be the same or different and are selected from —NO and —NO₂. Methods of preparing these compounds are also disclosed.

12 Claims, No Drawings

1,3,3,5,7,7-HEXANITROPERHYDRO-1,5-DIAZOCINE, N-NITROSO ANALOGS THEREOF, AND PROCESSES FOR THEIR PREPARATION

BACKGROUND OF THE INVENTION

This invention relates to organic explosives and more particularly to high energy-density polynitroorganic explosives.

Currently, RDX (cyclotrimethylenetrinitramine) and HMX (cyclotetramethylenetetranitramine) are the principal fillers used in military explosives and propellants. While both are highly important high energy compounds it is believed that they do not possess the highest energy-density attainable with organic high energy compounds. In addition, both RDX and HMX have unfavorable burning characteristics (rate and pressure exponent).

Therefore, it would be desirable to provide new high energy, high density compounds as additives to explosive and propellant compositions.

SUMMARY OF THE INVENTION

Accordingly, an object of this invention is to provide novel organic compounds.

Another object of this invention is to provide new high density, high energy explosives.

A further object of this invention is to provide new energetic organic additives for explosive and propellant compositions.

These and other objects of this invention are accomplished by providing:

a compound of the formula

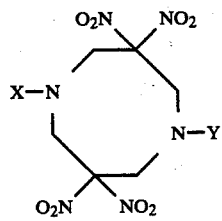

wherein x and y vary independently and are selected from the group consisting of —NO and —NO$_2$.

These compounds may be prepared by the following reaction sequences:

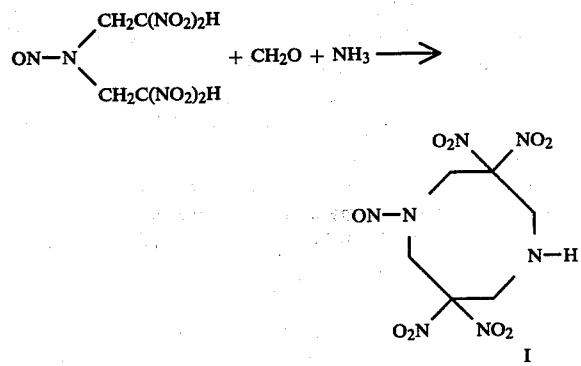

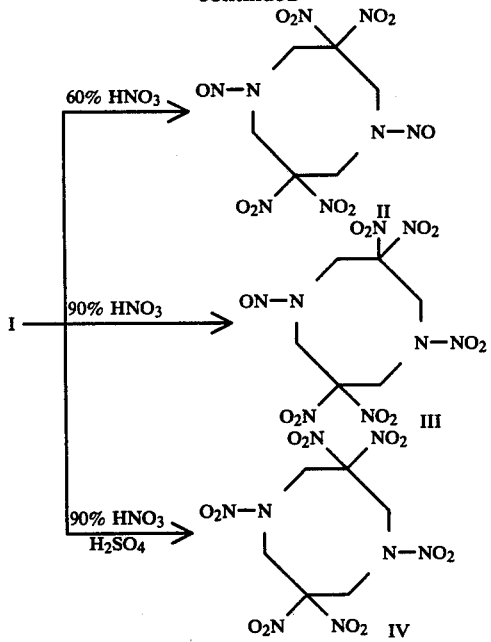

These compounds are useful as explosives and as energetic additives to explosives and propellants.

DESCRIPTION OF THE PREFERRED EMBODIMENT

The starting material 3,3,7,7-tetranitro-1-nitrosoperhydro-1,5-diazocine is prepared by reacting bis(dinitroethyl)nitrosoamine, formaldehyde, and ammonia in aqueous solution:

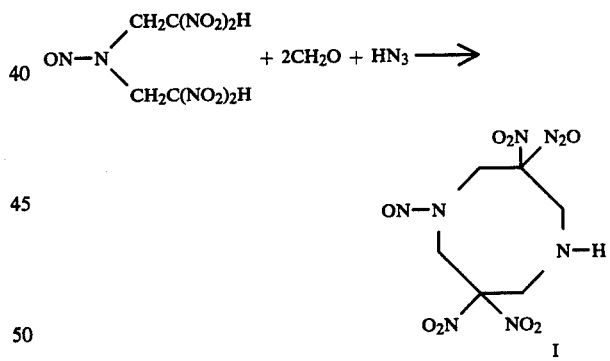

The bis(2,2-dinitroethyl)nitrosoamine is dissolved in a solution of water and a low molecular weight alcohol such as ethanol or preferably methanol. The alcohol serves to increase the solubility of the nitrosoamine in water. Aqueous solutions of formaldehyde and ammonia are then added. Acetic acid is added to the reaction mixture to lower the pH until a solid begins to form (pH 4). The reaction is carried out at ambient temperature (about 15° C. to about 25° C.).

The solid product 3,3,7,7-tetranitro-1-nitrosoperhydro-1,5-diazocine is filtered from the aqueous solution and recrystallized as illustrated in example 1.

3,3,7,7-tetranitro-1,5-dinitrosoperhydro-1,5-diazocine (II) is prepared by heating 3,3,7,7-tetranitro-1-nitrosoperhydro-1,5-diazocine (I) in from about 55 to about 70 percent HNO$_3$ at about 40° to about 45° C. for a few minutes. The product II can be purified by recrystallization from nitromethane.

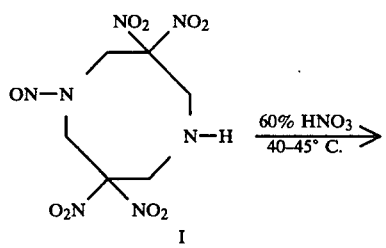

Example 2 illustrates this procedure.

3,3,5,7,7-Pentanitro-1-nitrosoperhydro-1,5-diazocine (III) is prepared by adding 3,3,7,7-tetranitro-1-nitrosoperhydro-1,5-diazocine, I, to a mixture of acetic anhydride and 90% HNO3 (oxide free) which is kept at 0° to 5° C. After about 10 minutes, the reaction mixture is poured onto ice. The product III can be purified by recrystallization from nitromethane.

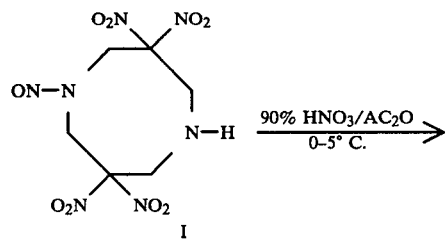

Example 3 illustrates this procedure.

1,3,3,5,7,7-hexanitroperhydro-1,5-diazocine (IV) is prepared by using a 90% nitric acid/concentrated sulfuric acid mixture at 0° to 5° C. to nitrate 3,3,7,7-tetranitro-1-nitrosoperhydro-1,5-diazocine.

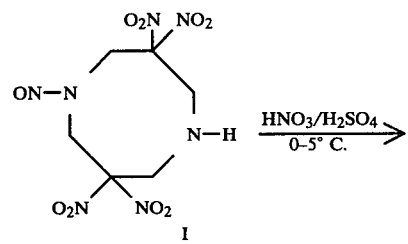

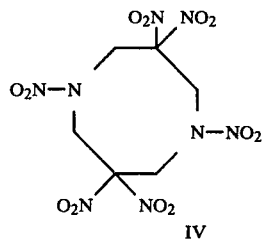

The procedure is illustrated by example 4.

The general nature of the invention having been set forth, the following examples are presented as specific illustrations thereof. It will be understood that the invention is not limited to these examples but is susceptible to various modifications that will be recognized by one of ordinary skill in the art.

EXAMPLE 1

Preparation of 3,3,7,7-Tetranitro-1-nitrosoperhydro-1,5-diazocine (I)

To 14.0 g bis(2,2-dinitroethyl)nitrosamine was added 216 ml 60 percent aqueous methanol and 6.4 g acetic acid. To this mixture was then added, at 15°-20° C., 12.9 ml aqueous ammonia (29 percent) in 13 ml water followed by 16.8 ml aqueous formaldehyde (37 percent). The pH was then adjusted to four with acetic acid. Solid starting forming as the pH was adjusted. The mixture was stirred overnight at room temperature. The solid was then filtered off, washed with water, and dried in a vacuum desiccator to give 13.8 g (81 percent) of 3,3,7,7-Tetranitro-1-nitrosoperhydro-1,5-diazocine. The product was recrystallized from methylene chloride/hexane, mp: 148° C. onset of decomposition, 159.50°-160.5° C. melts with decomposition; $^1$H NMR (CDCl3/acetone-d6): δ 3.0–3.3 (1H), 3.60 (d, 2H), 4.0 (d, 2H), 4.97 (s, 2H), 5.83 (s, 2H).

Analysis:

Calculated for: $C_6H_9N_7O_9$: C, 22.30; H, 2.81; N, 30.34. Found: C, 22.66; H, 2.85; N, 30.54.

EXAMPLE 2

Preparation of 3,3,7,7-Tetranitro-1,5-dinitrosoperhydro-1,5-diazocine (II)

To 7.0 ml 60 percent nitric acid at 40°-45° C. was added 0.2 g 3,3,7,7-tetranitro-1-nitrosoperhydro-1,5-diazocine (I). The mixture was heated at 40°-45° C. for five minutes and was then poured into ice. The solid was filtered off, washed with water and dried in a vacuum desiccator to give 0.109 g solid 3,3,7,7-Tetranitro-1,5-dinitrosoperhydro-1,5-diazocine. The solid was recrystallized from nitromethane to remove a small amount of starting material; mp: 190° C., onset of decomposition; 228°-229° C. melts; $^1$H NMR (acetone-d6): δ 4.81 (s), 5.26 (s), 5.73 (s), 6.16 (s).

Analysis:

Calculated for: $C_6H_8N_8O_{10}$: C, 20.46; H, 2.29; N, 31.82. Found: C, 20.45; H, 2.35; N, 31.62.

EXAMPLE 3

Preparation of 3,3,5,7,7-Pentanitro-1-nitrosoperhydro-1,5-diazocine (III)

To 5 ml acetic anhydride at 0°–5° C. was added 1.5 ml oxide-free nitric acid (90 percent). To this was added 0.2 g 3,3,7,7-tetranitro-1-nitrosoperhydro-1,5-diazocine (I). The mixture was stirred at 0°–5° C. for ten minutes and then was poured onto ice. The solution was stirred at room temperature for one hour. The solid was filtered off, washed with water, and dried in a vacuum desiccator. The solid was recrystallized from nitromethane to give 0.22 g (79 percent) of 3,3,5,7,7-pentanitro-1-nitrosoperhydro-1,5-diazocine, mp: 229° C., onset of decomposition; $^1$H NMR (acetone-$d_6$): $\delta$ 5.32, 5.37 (2s, 4H); 5.73 (s, 2H); 6.20 (s, 2H).

Analysis:

Calculated for: $C_6H_8N_8O_{11}$: C, 19.57; H, 2.19; N, 30.44. Found: C, 19.42; H, 2.29; N, 30.13.

EXAMPLE 4

Preparation of 1,3,3,5,7,7-hexanitropherhydro-1,5-diazocine (IV)

To 3.4 ml concentrated sulfuric acid at 0°–5° C. in an ice bath was added 0.075 g 3,3,7,7-tetranitro-1-nitrosoperhydro-1,5-diazocine (I). To this was then added a mixture of 0.8 ml nitric acid (90 percent) and 1.4 ml concentrated sulfuric acid. The mixture was stirred in the ice bath for 15 minutes and then was poured onto ice. The solid was filtered off, washed with water, and dried in a vacuum desiccator to give 0.080 g (90 percent) of 1,3,3,5,7,7-hexanitroperhydro-1,5-diazocine. The product was recrystallized from acetonitrile or nitromethane; mp: 250° C., onset of decomposition; $^1$H NMR (acetone-$d_6$): $\delta$ 5.70 (s).

Analysis:

Calculated for: $C_6H_8N_8O_{12}$: C, 18.75; H, 2.08; N, 29.17. Found: C, 19.04; H, 2.07; N, 28.96.

Obviously, numerous modifications and variations of the present invention are possible in light of the above teachings. It is therefore to be understood that within the scope of the appended claims the invention may be practiced otherwise than as specifically described herein.

We claim:

1. A nitroorganic compound of the formula

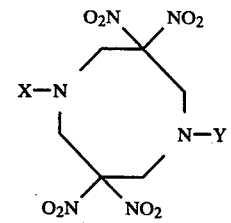

wherein x and y vary independently and are selected from the group consisting of —NO and —NO$_2$.

2. The compound of claim 1 which is 3,3,7,7-tetranitro-1,5-dinitrosoperhydro-1,5-diazocine.

3. The compound of claim 1 which is 3,3,5,7,7-pentanitro-1-nitrosoperhydro-1,5-diazocine.

4. The compound of claim 1 which is 1,3,3,5,7,7-hexanitroperhydro-1,5-diazocine.

5. A process for preparing 3,3,7,7-tetranitro-1-nitrosoperhydro-1,5-diazocine comprising the following steps:
   (1) forming an aqueous solution of
      (a) ammonia,
      (b) formaldehyde, and
      (c) bis(2,2-dinitroethyl)nitrosamine;
   (2) lowering the pH of the solution until the solid 3,3,7,7-tetranitro-1-nitrosoperhydro-1,5-diazocine product is formed; and
   (3) isolating the product.

6. The process of claim 5 wherein a low molecular weight water soluble alcohol selected from the group consisting of methanol, ethanol, and mixtures thereof is used to increase the solubility of bis(2,2-dinitroethyl)nitrosamine in the aqueous solution.

7. The process of claim 5 wherein acetic acid is used to lower the pH of the aqueous solution in step (2).

8. The process of claim 5 wherein the pH of the aqueous solution is adjusted to about 4 in step (2).

9. The process of claim 5 further comprising the steps thereafter of:
   (4) nitrosating the 3,3,7,7-tetranitro-1-nitrosoperhydro-1,5-diazocine in from about 55 to about 70 percent nitric acid to form 3,3,7,7-tetranitro-1,5-dinitrosoperhydro-1,5-diazocine product; and
   (5) isolating the 3,3,7,7-tetranitro-1,5-dinitrosoperhydro-1,5-diazocine.

10. The process of claim 9 wherein the nitrosation is performed at a temperature of from about 40° C. to about 45° C.

11. The process of claim 5 further comprising the steps thereafter of:
   (4) nitrating the 3,3,7,7-tetranitro-1-nitrosopehydro-1,5-diazocine in a mixture of acetic anhydride and 90% nitric acid at a temperature of from about 0° C. to about 5° C. to form 3,3,5,7,7-pentanitro-1-nitrosoperhydro-1-5-diazocine; and
   (5) isolating the 3,3,57,7-pentanitro-1-nitrosoperhydro-1,5-diazocine.

12. The process of claim 5 further comprising the steps thereafter of:
   (4) nitrating the 3,3,7,7-tetranitro-1-nitrosoperhydro-1,5-diazocine in a mixture of concentrated sulfuric acid and 90% nitric acid at a temperature of from about 0° C. to about 5° C. to form 1,3,3,5,7,7-hexanitroperhydro-1,5-diazocine; and
   (5) isolating the 1,3,3,5,7,7-hexanitroperhydro-1,5-diazocine.

* * * * *